United States Patent [19]

Blackwood et al.

[11] 4,089,900

[45] May 16, 1978

[54] ANTIMICROBIAL AGENTS

[75] Inventors: Robert K. Blackwood, Gales Ferry; Charles R. Stephens, Jr., East Lyme, both of Conn.

[73] Assignee: Pfizer Inc., New York, N.Y.

[21] Appl. No.: 720,145

[22] Filed: Sep. 3, 1976

Related U.S. Application Data

[60] Division of Ser. No. 325,628, Jan. 22, 1973, which is a division of Ser. No. 114,038, Feb. 9, 1971, Pat. No. 3,824,285, which is a division of Ser. No. 667,357, Sep. 13, 1967, Pat. No. 3,622,627, which is a continuation-in-part of Ser. No. 360,435, Apr. 16, 1964, abandoned, which is a continuation-in-part of Ser. No. 247,874, Dec. 28, 1962, abandoned.

[51] Int. Cl.$^2$ .................................. C07C 103/19
[52] U.S. Cl. .................. 260/559 AT; 260/552 SC; 260/554; 544/380
[58] Field of Search .................. 260/559 AT, 268 PT, 260/554, 552 SC

[56] References Cited

U.S. PATENT DOCUMENTS 3,183,267  5/1965  Blackwood et al. ......... 260/559 AT
3,200,149  8/1965  Blackwood et al. ......... 260/559 AT

OTHER PUBLICATIONS

Blackwood et al., J. Am. Chem. Soc., 83, (1961), pp. 2773–2775.

*Primary Examiner*—Arthur P. Demers
*Attorney, Agent, or Firm*—Connolly and Hutz

[57] ABSTRACT

4-Dedimethylaminotetracyclines and the corresponding 5a,6-anhydro derivatives having an oxo, hydroxy, substituted imino, amino or substituted amino group other than dimethylamino at the C-4-position useful as antimicrobial agents. The 4-oxo-4-dedimethylaminotetracyclines are prepared by oxidation of tetracyclines with a hydrocarbon dicarboxylic acid haloimide and then converted by reduction to the corresponding 4-hydroxy compounds or by reaction with a primary amine to 4-substituted imino derivatives. The latter compounds are reduced to 4-amino derivatives which are reductively methylated or alkylated to 4-substituted-4-dedimethylaminotetracyclines. Dehydration of the tetracycline compounds affords the corresponding 5a,6-anhydro compounds.

2 Claims, No Drawings

ANTIMICROBIAL AGENTS

CROSS-REFERENCE TO RELATED APPLICATIONS

This application is a division of application Ser. No. 325,628 filed Jan. 22, 1973, which, in turn, is a division of application Ser. No. 114,038 filed Feb. 9, 1971 and now U.S. Pat. No. 3,824,285, which, in turn, is a division of application Ser. No. 667,357 filed Sept. 13, 1967 and now U.S. Pat. No. 3,622,627, which, in turn, is a continuation-in-part of application Ser. No. 360,435 filed Apr. 16, 1964 and now abandoned, which, in turn, is a continuation-in-part of application Ser. No. 247,874 filed Dec. 28, 1962 and now abandoned.

BACKGROUND OF THE INVENTION

This invention is concerned with new and useful antimicrobial agents, and more particularly with novel 4-oxo-4-dedimethylamino derivatives of the tetracycline antibiotics and certain novel products obtained therefrom.

The tetracycline antibiotics comprise a group of biologically active hydronaphthacene derivatives having the following essential structural features:

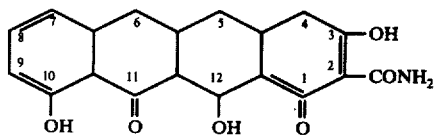

Among the biologically active members of this group are the following:

| Substituents | Common Name |
|---|---|
| 4-N(CH$_3$)$_2$,6-OH,6-CH$_3$,12a-OH | Tetracycline |
| 4-N(CH$_3$)$_2$,5-OH,6-OH,6-CH$_3$,12a-OH | 5-Oxytetracycline |
| 4-H(CH$_3$)$_2$,6-OH,6-CH$_3$,7-Cl,12a-OH | 7-Chorotetracycline |
| 4-5(CH$_3$)$_2$,5-OH,6-CH$_3$,12a-OH | 6-Deoxy-5-oxytetracyline |
| 4-N(CH$_3$)$_2$,6-CH$_3$,12a-OH | 6-Deoxytetracyline |
| 4-N(CH$_3$)$_2$,12a-OH | 6-Deoxy-6-demethyltetracyline |
| 4-N(CH$_3$)$_2$,6-OH,6-CH$_3$,7-Br,12a-OH | 7-Bromotetracycline |
| 4-N(CH$_3$)$_2$,6-OH,7-Cl,12a-OH | 6-Demethyl-7-chlortetracycline |
| 4-N(CH$_3$)$_2$,6-OH,12a-OH | 6-Demethyltetracycline |
| 4-N(CH$_3$)$_2$,6-(=CH$_2$),12a-OH | 6-Methylenetetracycline |
| 4-N(CH$_3$)$_2$,6-(=CH$_2$),11a-Cl,12a-OH | 11a-Chloro-6-methylenetetracycline |
| 4-N(CH$_3$)$_2$,5-OH,6-(=CH$_2$),12a-OH | 6-Methylene-5-oxytetracycline |
| 4-N(CH$_3$)$_2$,5-OH,6-(=CH$_2$),11a-Cl,12a-OH | 11a-Chloro-6-methylene-5-oxytetracycline |

SUMMARY OF THE INVENTION

The novel compounds of the present invention have the general formulae:

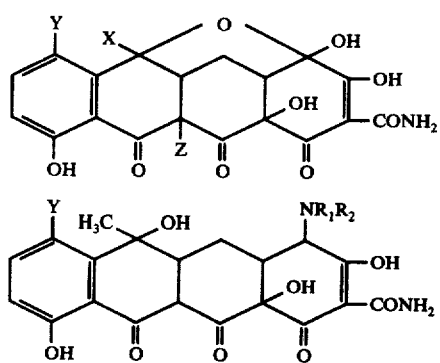

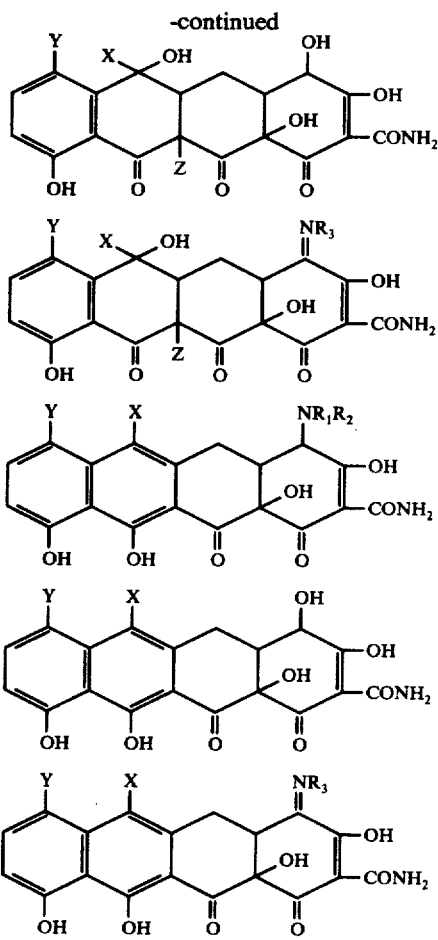

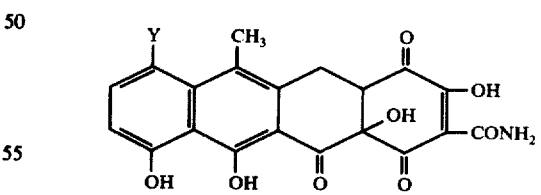

wherein R$_1$ is selected from the group consisting of hydrogen, benzyl, phenethyl, cyclohexyl and alkyl of from 2 to 6 carbon atoms; R$_2$ is selected from the group consisting of hydrogen, alkyl of from 2 to 6 carbon atoms and hydroxyalkyl of from 2 to 4 carbon atoms; R$_3$ is selected from the group consisting of OH, NHCONH$_2$, NHC(NH)NH$_2$, NHCSNH$_2$, 4($\beta$-hydroxyethyl)piperazino, and NR$_4$R$_5$ wherein R$_4$ is selected from the group consisting of hydrogen, alkyl of from 1 to 6 carbon atoms, phenyl, benzyl and cyclohexyl; R$_5$ is selected from the group consisting of hydrogen, alkyl of from 1 to 6 carbon atoms which may be straight-chained or branched-chained, phenyl, and benzyl;

Z is selected from the group consisting of hydrogen, chloro and fluoro;

X is selected from the group consisting of methyl and hydrogen, with the proviso that X is methyl when Z is hydrogen;

Y is selected from the group consisting of hydrogen and chloro.

A preferred member of this class of derivatives is 4-oxo-4-dedimethylaminotetracycline-4,6-hemiketal, having the structure I. The hemiketal structures of this invention exist in equilibrium with the equivalent non-ketalized form, II.

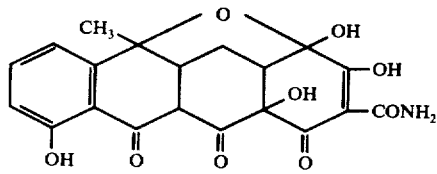

I

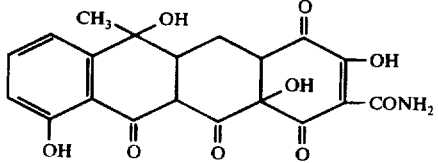

II and wherever 4,6-hemiketals are referred to herein and in the appended claims, the term is intended to embrace the corresponding nonketalized form as well.

The reaction sequences employed in the preparation of the compounds of the present invention are exemplified in the following flowsheet using tetracycline as the reactant.

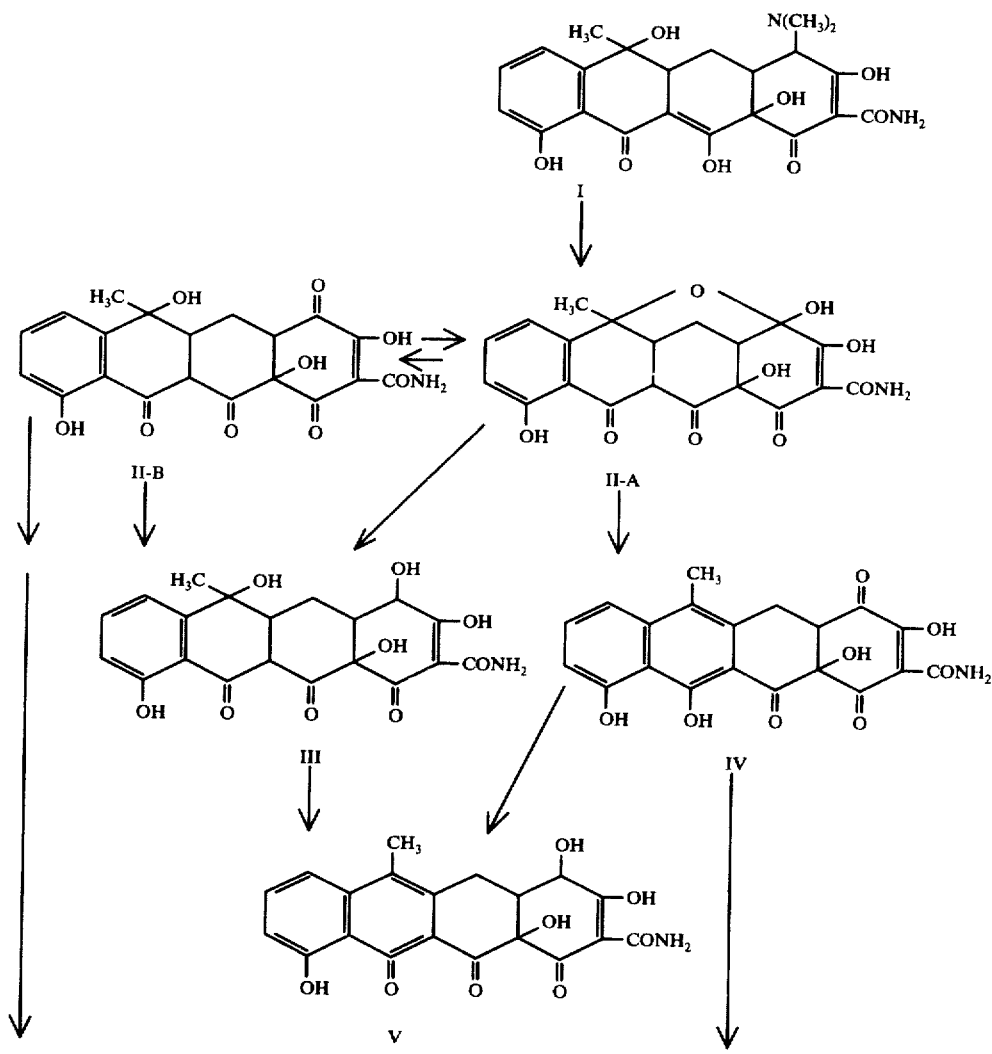

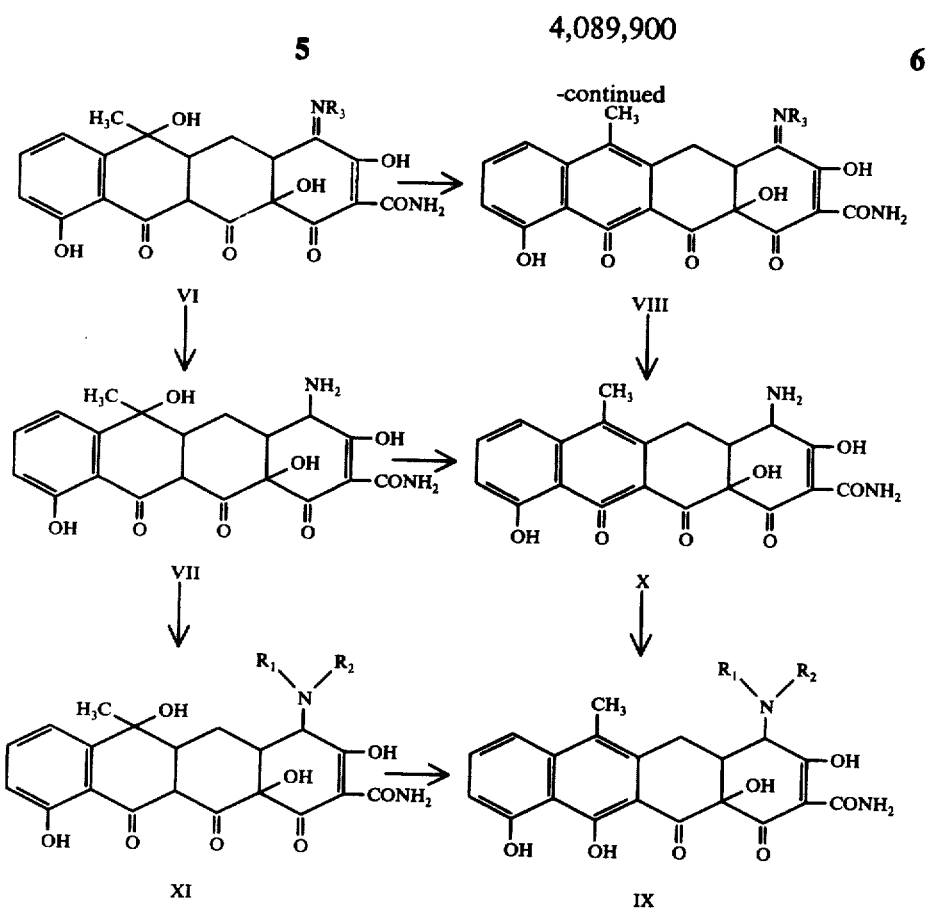

DETAILED DESCRIPTION OF THE INVENTION

In this reaction sequence $R_1$, $R_2$ and $R_3$ are as defined above.

I → II-A represents an oxidation reaction.

II-A or II-B → III and

IV → V represent reductions of the 4-oxo group to 4-hydroxy.

III → V, VII → X, XI → IX and

II-A or II-B → IV represent dehydration reactions to form 5a,6-anhydro compounds.

II-A or II-B → VI and IV → VIII represent reaction with carbonyl group reagents.

VI → VII and VIII → X represent reduction reactions.

VII → XI and X → IX represent alkylations.

The oxidation reaction to form a 4,6-hemiketal may be effected under acid conditions by treating a compound of the formula:

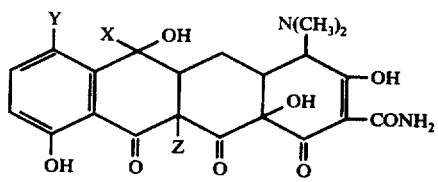

wherein X and Z have the above significance with a hydrocarbon dicarboxylic acid haloimide such as N-chlorosuccinimide, preferably in aqueous media and at pH below 2. Dilute mineral acid such as dilute hydrochloric acid is a preferred medium. The reaction is readily carried out at room temperature, and the product may be recovered by filtration and purified by such methods as solvent extraction, treatment with activated carbon, and precipitation in the form of a metal salt, e.g. an alkali metal or alkaline earth metal salt. The equilibrium between the hemiketal and the non-ketalized form is shifted in favor of the hemiketal in the crystalline state and in acid media; under basic conditions the equilibrium appears to shift toward the non-ketalized form, although under extremely basic conditions this is accompanied by degradation. Thus, prolonged treatment with liquid ammonia or aqueous potassium hydroxide at about pH 12 leads to the formation of compounds such as the following.

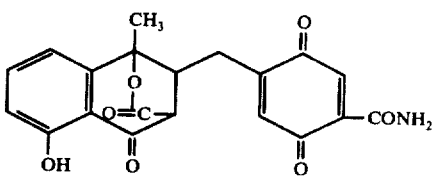

Application of the described N-chlorsuccinimide treatment to 11a-halotetracycline-6,12-hemiketals having the following formula:

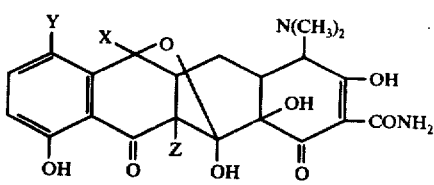

wherein X, Y and Z are as defined above, provides 4-oxo-4-dedimethylamino-11a-halotetracycline-4,6- hemiketals; 6-deoxy-6-demethyltetracycline and 11a-chloro-6-methylenetetracycline yield similar non-basic products under these conditions.

The reduction reactions to produce a 4-hydroxy group may be carried out at room temperature by various means, including treatment with sodium hydrosulfite, zinc dust in dilute mineral acid or aqueous acetic acid, or mild catalytic hydrogenation. A preferred procedure entails treatment with an alkali metal hydrosulfite such as sodium hydrosulfite in a suitable solvent, e.g. aqueous alcohol, followed by recovery and purification by such methods as solvent extraction and recrystallization.

The dehydration reactions to produce 5a,6-anhydro compounds are effected by treatment in solution with mineral acid such as concentrated hydrochloric acid or paratoluene sulfonic acid, suitably in a solvent such as acetone or methanol, and conveniently at elevated temperature, e.g. 80°–100° C., to accelerate the desired conversion. Alternatively, the reaction may be conducted in liquid hydrogen fluoride, in which case it is more convenient to carry out the conversion at a temperature below the atmospheric boiling point e.g. 0°–10° C. The anhydro products are readily recovered by precipitation from the reaction mixture where solubility is limited, or alternatively by evaporation of the reaction medium.

The 4-hydroxy-5a,6-anhydrotetracyclines of the present invention are characterized by excellent stability and exhibit surprisingly high biological activity against various microorganisms, including antibiotic-resistant strains. For example, 4-hydroxy-4-dedimethylamino-5a,6-anhydrotetracycline, when tested in vitro by the usual serial dilution technique, exhibits the following minimum inhibitory concentrations against various disease-causing microorganisms:

| Species | M.I.C. (mcg./ml.) |
| --- | --- |
| Micrococcus pyogenes var. aureus | 12.5 |
| Micrococcus pyogenes var. aureus 400* | 25 |
| Streptococcus pyogenes | 3.12 |
| Streptococcus pyogenes 98 | 1.56 |
| Streptococcus faecalis | 12.5 |
| Diplococcus pneumoniae | 25 |
| Erysipelothrix rhusiopathiae | 6.25 |
| Escherichia coli | 25 |
| Salmonella typhosa | 12.5 |
| Klebsiella pneumoniae | 25 |
| Hemophilus influenzae | 50 |

*Antibiotic resistant strain

As will be seen from the above data, these novel anhydrotetracyclines are useful in therapy, in agriculture, and in veterinary practice both therapeutically and as growth stimulants. In addition, they may be employed as disinfectants and bacteriostatic agents, in industrial fermentations to prevent contamination by sensitive organisms, and in tissue culture, e.g. for vaccine production. They are likewise useful in separating and classifying mixtures of microorganisms for biological research and medical diagnostic purposes.

The 4,6-hemiketal and the 4-oxo derivatives of this invention are useful intermediates for the introduction of new substituents at the 4 position of the tetracycline and anhydrotetracycline compounds. Thus, they may be subjected to reductive amination in the presence of reducing agents such as formic acid or its derivatives, or hydrogen together with noble metal catalysts, to introduce new 4-amino substituents. They may be reacted with various carbonyl group reagents, that is, reagents derived from ammonia which react rather generally with the carbonyl group of aldehydes and ketones. Typical of such reagents are those having the formula $H_2HR_3$ wherein $R_3$ is as defined above. Representative compounds are hydroxylamine, hydrazine, semicarbazide, phenylhydrazine, thiosemicarbazide, mono- and unsymmetrically disubstituted hydrazines.

The hydrazine and other carbonyl group reagents may be used as their acid salts or as the free bases. The lower alcohols are the preferred solvents, particularly when using the free bases as reagent. In certain solvents, ether for example, simple salt formation rather than reaction at the keto group occurs. However, since a wide variety of solvents are operative, the choice of solvent is readily determined by experiment on a small scale. The lower alcohols, methyl, ethyl, isopropyl, etc., or combinations thereof, are favored.

The resulting oximes, hydrazones, semicarbazones and thiosemicarbazones may be reduced to the corresponding saturated compounds under appropriate conditions, or to the 4-amino-4-dedimethylaminotetracyclines and 4-amino-4-dedimethylaminoanhydrotetracyclines.

Reductive amination may be conducted with ammonia and primary amines including monoalkanolamines, alkylamines of from 1 to 6 carbon atoms, benzylamine, β-phenethylamine, aniline and cyclohexylamine. The reaction is conducted in a suitable reaction-inert solvent system such as dimethylformamide at a temperature of from about 20° to about 50° C. Low pressures, that is, pressures of from about 1 atmosphere to about 150 atmospheres are preferred mostly for the sake of convenience. Higher pressures can be used but appear to offer no advantages. Platinum oxide is favored as catalyst since it produces satisfactory yields. Other catalysts such as Raney nickel may also be used. An excess of the ammonia or amine is used. The addition of the hydrochloride salt of ammonia or of the amine improves the yield in many instances.

It has been found advantageous, in order to minimize decomposition of the reactants and products, to use the tetracycline-4,6-hemiketal compounds in the form of a chelate of a polyvalent metal ion such as magnesium, calcium, zinc, copper, cobalt, nickel, manganese and cadmium. The metal chelate may be formed in situ, preferably by addition of a suitable solvent soluble salt, e.g. the polyvalent metal chloride, acetate, nitrate, etc., or may be preformed. A 1:1 molar ratio of polyvalent metal ion to tetracycline-4,6-hemiketal is preferred. The same considerations apply to the 4-oxo-5a,6-anhydrotetracyclines. The reductive amination product is regenerated from its metal chelate by known methods, e.g. acid treatment to decompose the chelate, ion-exchange treatment or precipitation of the chelated metal as an insoluble salt, such as the sulfide or oxalate.

Reductive amination of 4-oxo-4-dedimethylaminotetracycline-4,6-hemiketal with ammonium hydroxide in the presence of a polyvalent metal ion, e.g. magnesium, produces a mixture of 4-epi- and 4-normal-amino-4-dedimethylaminotetracycline in which the 4-epi compound predominates. Methylamine under similar conditions produces predominately the 4-epi compound, 4-epi-4-methylamino-4-dedimethylaminotetracycline. The other amines mentioned above also produce the 4-epi compound as major product.

Chemical and catalytic reduction of the compounds bearing a $=YR_3$ group at the 4-position to 4-amino-4- dedimethylaminotetracyclines also produces a mixture of the 4-epi- and 4-normal-amino-4-dedimethylaminotetracyclines in which the 4-epi compound predominates. The 4-normal compounds exhibit much greater antibacterial activity than do the 4-epi compounds. The formulae used herein are intended to embrace the epi- and normal configurations at the C.4 position.

The 4-amino-4-dedimethylaminotetracycline (the 4-normal compound referred to above) is isolated from the mixture containing the 4-epi compound by warming the mixture in mild basic solution, e.g. aqueous sodium or potassium bicarbonate, whereby the 4-epi compound is degraded. The normal 4-aminotetracycline is recovered by suitable means as by solvent extraction. This method is applicable to the isolation of the 4-normal-monosubstituted-amino-4-dedimethylaminotetracyclines in general. The novel 4-amino-4-dedimethylaminotetracyclines and anhydrotetracyclines of this invention (epi and normal configuration) may be alkylated in a suitable solvent system (tetrahydrofuran or acetone) by means of appropriate agents such as alkyl, alicyclic and aralkyl iodides and dialkyl sulfates. The use of an acid acceptor (inorganic or organic base) or acid scavenger (propylene oxide) is required to promote dialkylation. The use of excess alkyl, alicyclic or aralkyl iodide plus acid acceptor or scavenger in any of these alkylations leads to betaine formation.

They may also be reductively alkylated using an aldehyde or ketone in the presence of a reducing agent such as hydrogen and a catalyst, e.g. Raney nickel or platinum. Lower alkanols, especially methanol or ethanol are favored solvent systems. Hydrogen pressures of from about 1 to 150 atmospheres and temperatures of from about 20°-80° C. are suitable.

The 4-hydroxy-4-dedimethylaminotetracyclines, while surprisingly possessing negligible in vitro biological activity against a variety of Gram-positive and Gram-negative microorganisms tested, are useful intermediates, and may be converted to readily replaceable sulfonic esters such as the tosylates, which may in turn be employed in nucleophilic replacement reactions, e.g. with amines, mercaptans, cyanides and the like to introduce $C_4$ substituents.

Also included in this invention are compounds having the formulae:

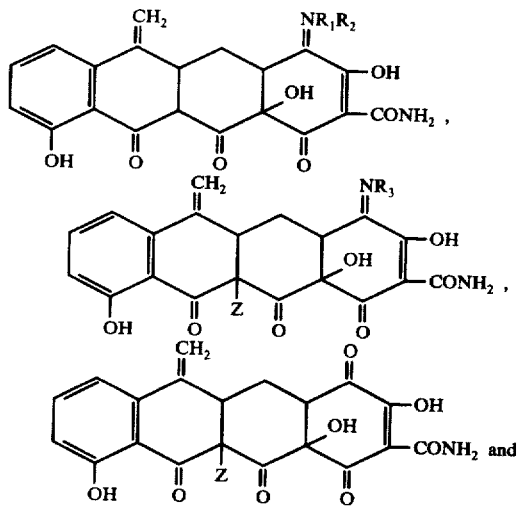

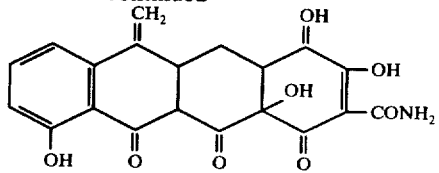

wherein $R_1$, $R_2$ and Z are as previously defined and $R_3$ is selected from the group consisting of OH, $NHCONH_2$, $NHC(NH)NH_2$, 4-($\beta$-hydroxyethyl)piperazine, and $NR_4R_5$ wherein $R_4$ is selected from the group consisting of hydrogen, alkyl of from 1 to 6 carbon atoms, phenyl, benzyl and cyclohexyl and $R_5$ is selected from the group consisting of hydrogen, alkyl of from 1 to 6 carbon atoms, phenyl and benzyl. A preferred compound is of the first of the above formulae wherein $R_1$ and $R_2$ are hydrogen.

The present invention embraces all metal salts of the new products and all acid addition salts of the new basic products described herein. The well-known procedures for preparing salts of tetracycline compounds are applicable here and are illustrated by examples appearing hereinafter. Such salts may be formed with pharmaceutically acceptable and pharmaceutically unacceptable metals and acids. By "pharmaceutically acceptable" is meant those salt-forming metal ions and acids which do not substantially increase the toxicity of the tetracycline compound. Of particular value in the case of the therapeutically active tetracyclines are the pharmaceutically acceptable metal and acid addition salts. In the case of the compounds herein described which are primarily useful as intermediates, the most useful salts are the alkali and alkaline-earth metal salts.

The pharmaceutically acceptable metals include sodium, potassium and alkaline-earth metals of atomic number up to and including 20, i.e. magnesium and calcium, and additionally aluminum, zinc, iron and manganese, among others. Of course, the metal salts include complex salts, i.e. metal chelates, which are well recognized in the tetracycline art. The pharmaceutically unacceptable metal salts embrace most commonly salts of lithium and of alkaline-earth metals of atomic number greater than 20, i.e. barium and strontium, which are useful for isolating and purifying the compounds. The new substances also form salts with amines of sufficient basicity.

The pharmaceutically acceptable acid addition salts are of particular value in therapy. These include salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g. p-toluenesulfonic acids, and the like. The pharmaceutically unacceptable acid addition salts, while not useful for therapy, are valuable for isolation and purification of the new substances. Further, they are useful for the preparation of pharmaceutically acceptable salts. Of this group, the more common salts include those formed with hydrofluoric and perchloric acids. Hydrofluoride salts are particularly useful for the preparation of the pharmaceutically acceptable salts, e.g. the hydrochlorides, by solution in hydrochloric acid and crystallization of the hydrochloride salt formed. The perchloric acid salts are useful for purification and crystallization of the new products.

The herein described compounds are useful as complexing agents for polyvalent metal ions. The complexes are usually quite soluble in organic solvents and are useful for purposes wherein metal ion contamination is a problem: e.g. stabilizers in fatty acids, waxes, hydrocarbons, biological experimentation, metal extraction, and as metal carriers.

The following examples are provided for illustrative purposes.

EXAMPLE I

4-Oxo-4-Dedimethylaminotetracycline-4,6-Hemiketal

A. The tetracycline hydrochloride, 70 g., is dissolved with stirring in a mixture of 14 ml. concentrated hydrochloric acid and 3500 ml. water. To this is added 49 g. N-chlorsuccinimide. After stirring for 1 hour the reaction mixture is filtered and the solid is washed thoroughly with water and air-dried to obtain 47.1 g. of the desired product.

For purification, 21.0 g. of this material is dissolved with stirring at room temperature in 420 ml. water plus 1300 ml. ether. The water layer is discarded and the ether is washed with 5 × 130 ml. portions of water. After drying over sodium sulfate, the ether solution is evaporated to an oil. About 300 ml. water is added and the mixture stirred for 2 hours and filtered. Water-washing and air-drying yield 17.5 g. of partially purified solid.

Further purification is achieved by conversion to the potassium salt in the following manner: 1.0 g. of this product is dissoled in 4.0 ml. methanol at room temperature with stirring. This solution is treated with Darco G-60 activated carbon, filtered and the filtrate treated with 0.40 ml. 5N potassium hydroxide aqueous solution (1 millimole). This mixture is stirred for 15 minutes at room temperature, filtered, and the recovered solid is methanol-washed and dried under vacuum.

ANALYSIS

Found: C, 51.96; H, 3.83; N, 3.22; K, 8.18; $H_2O$, 1.71. Calcd. for $C_{20}H_{16}O_9NK.0.5H_2O$: C, 52.0%; H, 3.8; N, 3.2; K, 8.2; $H_2O$, 1.7.

This product exhibits ultraviolet absorption maxima in 0.01 N methanolic HCl at 268 and 346 m$\mu$, log $\epsilon$ 4.40 and 3.72, and an infrared absorption maximum in potassium bromide at 5.7 $\mu$. In 0.01 N methanolic NaOH decomposition appears to occur, but fresh solutions exhibit ultraviolet absorption maxima at about 265, 319 and 372 m$\mu$.

The sodium salt is prepared in the same manner, substituting sodium hydroxide for potassium hydroxide.

B. An attempt to prepare the title compound by air oxidation of tetracycline produced no detectable amount of the compound.

A solution of tetracycline (1 g.) in dimethylformamide (30 ml.) is exposed to air at room temperature for ten days then evaporated to dryness under reduced pressure. The residue is slurried in 25 ml. of 0.1 N hydrochloric acid, and the insoluble material collected by filtration (0.66 g.).

Treatment of the crude product with sodium hydrosulfite failed to produce the fluorescent 4-hydroxy compound in contrast to the 4-oxo compound produced in Method A. It is concluded that no 4-oxo-4-dedimethylaminotetracycline-4,6-hemiketal is produced by air oxidation.

EXAMPLE II

4-Oxo-11a-Chloro-4-Dedimethylaminotetracycline-4,6-Hemiketal

11a-Chlortetracycline-6-,12-hemiketal, 20.5 g., is combined with a solution of 6.3 ml. concentrated hydrochloric acid in 1025 ml. water and 14.5 g. N-chlorsuccinimide is added. After stirring 1 hour at room temperature the reaction mixture is filtered and the 10.8 g. of solid product water-washed and dried.

This substance is further purified by extraction with a mixture of 255 ml. water plus 631 ml. ether. The water layer is then re-extracted with 350 ml. ether, and the ether layers are combined, washed with 3 × 50 ml. volumes of water and 2 × 50 ml. volumes of saturated brine. The ether is evaporated. The resulting crystalline solid is slurried with 15 ml. methanol, and 6.2 g. solid product recovered by filtration. It exhibits infrared absorption maxima at 5.77, 6.02, 6.32 and 6.55 $\mu$; ultraviolet absorption maxima occur at 258 and 343 m$\mu$ in 0.01 N methanolic HCl, log $\epsilon$ 4.42 and 3.68, respectively.

ANALYSIS

Found: C, 53.0; H, 3.7; N, 2.8; Cl, 8.0. Calcd. for: $C_{20}H_{16}O_9NCl$: C, 53.4; H, 3.6; N, 3.1; Cl, 7.9.

The starting compound for this reaction is prepared in the following manner:

To a solution of 2.2 g. anhydrous tetracycline in 25 ml. ethylene glycol dimethylether is added 800 mg. N-chlorsuccinimide with stirring to dissolve the reagent. The mixture is allowed to stand for 7 minutes and then diluted with 25 ml. water. The product, 873 mg., crystallizes as white needles. Infrared analysis shows no carbonyl bands between 5 and 6 $\mu$.

It is purified further by stirring for 20 minutes in 15 ml. methanol. Infrared absorption maxima are exhibited at the following wave lengths when measured in a XBr pellet at 1% concentration: 2.93, 5.70, 6.02, 6.32, 6.55, 7.15, 7.25, 7.47, 7.58, 7.87, 8.08, 8.19, 8.41, 8.50, 9.05, 9.52, 9.82, 10.04, 10.41, 10.95, 11.54, 11.77, 12.12, 12.32, 12.50, 12.80, 13.28, 13.47 $\mu$. The ratio of $B_{1\ cm}^{1\%}$ values measured in 0.01 N methanolic-HCl at 261 and 345 ml. is 5.6.

By means of this procedure the following 4-oxo-4-dedimethylaminotetracycline-4,6-hemiketals are prepared from the appropriate tetracycline compound.

| Y | X | Z |
|---|---|---|
| H | $CH_3$ | H |
| Cl | $CH_3$ | H |
| Cl | $CH_3$ | F |
| H | $CH_3$ | F |
| Cl | $CH_3$ | Cl |
| Cl | H | Cl |
| H | H | F |
| H | H | Cl |

The 11a-fluoro and chloro-tetracycline-6,12-hemiketal reactants are prepared according to the procedure of U.S. Pat. No. 3,109,007, issued Oct. 29, 1963.

EXAMPLE III

4-Hydroxy-4-Dedimethylaminotetracycline

Method A. The crude product of Example I, 25.0 g., is dissolved with stirring in 312.5 ml. methanol and to this is added a solution of 10 g. sodium hydrosulfite in 225 ml. water. After stirring at room temperature for 40 minutes, the reaction mixture is combined with 250 ml. water and 1250 ml. ether. The ether extract is separated and the aqueous layer re-extracted with another 1250 ml. fresh ether. The two ether layers are washed with water, for 1 hour, filtered and washed thoroughly with water to obtain 19.1 g. of the desired product.

For purification, 1.0 g. of this material is dissolved in 60 ml. ethylene dichloride with heating, and the solution is filtered. Upon cooling the filtrate crystallizes and the 200 mg. of crystalline product is separated by filtration. A second 200 mg. crop of light yellow-green crystals is obtained from the mother liquor. The product exhibits ultraviolet absorption maxima in 0.01 N methanolic HCl at 257 and 362 m$\mu$, log $\epsilon$ 4.23 and 4.20; in 0.01 N methanolic NaOH at 246, 264 and 377 m$\mu$ and in 0.01 N Mg Cl$_2$ at 259, 339 and 373 m$\mu$.

ANALYSIS

Found: C, 57.31; H, 4.57; N, 3.19. Calcd. for $C_{20}H_{19}NO_9$: C, 57.5; H, 4.45; N, 3.35.

Method B. The title product of Example II (500 mg.) is dissolved in 25 ml. ethyl acetate and hydrogenated over 10% Pd/C (50 mg.) at 1 atmosphere hydrogen and 25° C. until 2 molar equivalents of hydrogen are taken up. The catalyst is removed by filtration and the solvent stripped to give a yield of 450 mg.

Method C. Five hundred mg. of the title product of Example II, zinc dust (200 mg.) and 5 ml. of 50% aqueous acetic acid are stirred vigorously at room temperature for 15 minutes. The mixture is then filtered and the filtrate freeze-dried. Treatment of the residue with dilute hydrochloric acid yields free 4-hydroxy-4-dedimethylaminotetracycline.

The remaining products of Example II are reduced to the corresponding 4-hydroxy-4-dedimethylaminotetracyclines having the formula:

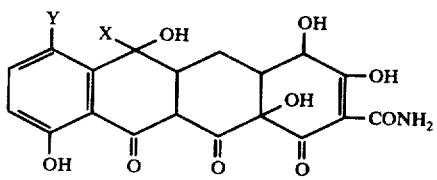

wherein Y and X have the values listed in Example II by the above procedures. The 11a-halogenated products of Example II are reduced by Methods B and C. To avoid removal of the 7-chloro group hydrogenation is terminated when 2 equivalents of hydrogen are consumed. Alternatively, rhodium is used as catalyst. The zinc dust-acetic acid system of Method C is replaced by zinc dust-mineral acid in the case of the 11a-fluoro compounds for more efficient reaction.

EXAMPLE IV

4-Hydroxy-4-Dedimethylamino-5a,6-Anhydrotetracycline

Method A. The title product of Example III, 500 mg., is dissolved at room temperature in 10 ml. methanol and the solution is filtered. To the filtrate is added 3 ml. concentrated hydrochloric acid and the mixture is heated on a steam bath until precipitation begins (about 3-5 minutes). The reaction mixture is then permitted to cool to room temperature and the desired solid product separated by filtration. The yield is 400 mg. of material exhibiting ultraviolet absorption maxima at 272 and 423 m$\mu$ in 0.01 N methanolic HCl.

Method B. The title product of Example III, 500 mg., is dissolved in 5.0 ml. hot acetone, 1.0 g. paratoluenesulfonic acid is then added and dissolved with further heating. The reaction mixture is treated with Darco KB activated carbon and filtered. The filtrate is then evaporated to an oil, which crystallizes. The orange crystalline solid is recovered by filtration, washed with a little acetone, and dried. The product exhibits $R_f$ values of 0.9 and 0.95, respectively, in the following systems:

| Mobile Phase | Stationary Phase |
| --- | --- |
| 20:3 by volume toluene:pyridine | pH 4.2 aqueous buffer |
| 20:10:3 by volume nitromethane:chloroform:pyridine | pH 3.5 aqueous buffer |

Elemental Analysis
Found: C, 59.82; H, 4.54; N, 3.26
Calcd. for C, 60.1; H, 4.3 ; N, 3.5
$C_{20}H_{17}O_8N$:

Ultraviolet absorption maxima are observed at 222, 262, 310 and 423 m$\mu$; log $\epsilon$ 4.46, 4.70, 3.68 and 4.01, respectively.

By means of these procedures the remaining products of Example III are converted to the corresponding 5a,6-anhydrotetracyclines.

EXAMPLE V

4-Oxo-4-Dedimethylamino-5a,6-Anhydrotetracycline

The product of Example I, 100 mg., is stirred in an ice-water bath with 2.0 ml. liquid hydrogen fluoride for 95 minutes. The hydrogen fluoride is then evaporated in a stream of nitrogen and the residue is stirred at room temperature with about 19 ml. dry ether for 45 minutes and then filtered and dried to obtain 37 mg. of the desired solid product. This substance is further convertible to the product of Example IV by treatment with sodium hydrosulfite according to the procedure of Example III. This reactivity is readily demonstrated by treating a 1 mg./ml. solution of the title product in 1:1 methanol:water with 10 mg./ml. sodium hydrosulfite; this solution may then be subjected to partition chromatography in 20:3 by volume toluene:pyridine on Whatman chromatographic paper saturated with pH 4.2 aqueous McIlvaine buffer. Whereas 4-oxo-4-dedimethylamino-5a,6-anhydrotetracycline in the absence of sodium hydrosulfite exhibits an orange spot at the origin in this system, in the presence of the sodium hydrosulfite a new spot appears corresponding to 4-hydroxy-4-dedimethylamino-5a,6-anhydrotetracycline at an $R_f$ value of about 0.9.

EXAMPLE VI

4-Hydrazone-4-Dedimethylaminotetracycline

A. A mixture of 15 g. of 4-oxo-4-dedimethylaminotetracycline-4,6-hemiketal, 61 ml. of methanol, 30 g. of potassium bicarbonate, and 5.7 g. of powdered hydrazine dihydrochloride is stirred for 30 minutes at room temperature. The reaction mixture is then filtered and washed with methanol. 900 ml. of water containing 6 ml. of concentrated hydrochloric acid is slowly added to the mother liquor with stirring and the mixture allowed to stand. The product which crystallizes over a 45-minute period is recovered by filtration, washed with water and dried to give 7.6 g. of product. It is purified by stirring for 2 hours in 3A ethanol and refiltered.

An analytical sample is obtained by recrystallization from tetrahydrofuran-water. The crystalline product is dried in vacuo at room temperature.

ANALYSIS

Found: C, 53.8; H, 4.6; N, 9.0. Calcd. for $C_{20}H_{19}N_3O_8 \cdot H_2O$: C, 53.7; H, 4.7; N, 9.4.

The product exhibits ultraviolet absorption maxima in 0.01 N methanolic-HCl at 264 and 335 m$\mu$, log $\epsilon$ 4.16 and 4.53, respectively. In 0.01 N methanolic-sodium hydroxide ultraviolet absorption maxima are exhibited at 261, 323 and 373 m$\mu$, log $\epsilon$ 4.33, 4.25 and 4.29, respectively.

B. Crude 4-oxo-4-dedimethylaminotetracycline-4,6-hemiketal (417 mg.) is dissolved in 3 ml. of 3A-ethanol and 0.06 ml. of hydrazine hydrate in 3.5 ml. of 3A-ethanol added over a 15-minute period with stirring. The mixture is stirred an additional 15 minutes, the crystalline 4-hydrazono product filtered, washed with 3A-ethanol and dried.

Substitution of hydrazine hydrate or its dihydrochloride salt of methods B and A by the appropriate carbonyl reagent produces the following 4-substituted-4-dedimethylaminotetracyclines. For convenience only the $R_3$ group of the C-4 substituent ($=NR_3$) is given.

| $R_3$ | $R_3$ | $R_3$ |
|---|---|---|
| —RNCH$_3$ | NHCONH$_2$ | N(C$_6$H$_5$)$_2$ |
| —HNC$_6$H$_5$ | NHCSNH$_2$ | CH$_3$NC$_6$H$_5$ |
| —N(CH$_3$)$_2$ | NHC(NH)NH$_2$ | C$_2$H$_5$NC$_6$H$_5$ |
| —RNCH$_2$C$_6$H$_5$ | NH(i-C$_{37}$) | N(sec-C$_4$H$_9$)$_2$ |
| HNC$_6$H$_{13}$ | CH$_3$N(i-C$_3$H$_7$) | (i-C$_3$H$_7$)(NC$_6$H$_5$ |
| HNC$_6$H$_{11}$ | CH$_3$N(n-C$_4$H$_9$) | |
| N(C$_2$H$_5$)$_2$ | C$_6$H$_5$NCH$_2$C$_6$H$_5$ | |
| HN(n-C$_4$H$_9$) | 1-[4-($\beta$-hydroxyethyl) piperazine] | |

The 4-oxotetracyclines of Example II are likewise treated with the same reagents to produce the corresponding compounds bearing the $=NR_3$ group at C.4.

C. Crude 4-oxo-11a-chloro-4-dedimethylaminotetracycline-4,6-hemiketal (450 mg.) is dissolved in 25 ml. of 3A-ethanol, treated with charcoal then filtered 0.05 ml. of hydrazine hydrate in 5 ml. of 3A-ethanol is added over a 15-minute period with stirring. The mixture is stirred 4 hours, treated with charcoal and filtered. The solution is evaporated to dryness and triturated with ether to give 170 mg. of product; 4-hydrazono-11a-chloro-4-dedimethylaminotetracycline.

By reduction of this product in 3A-ethanol with 5% palladium on charcoal as catalyst and limiting the hydrogen uptake to 1 equivalent 4-hydrazono-4-dedimethylaminotetracycline is produced.

EXAMPLE VII 5a,6-Anhydro-4-Hydrazono-4-Dedimethylaminotetracycline

4-Hydrazono-4-dedimethylaminotetracycline (3.4 g.) is dissolved in 68 ml. of methanol-concentrated hydrochloric acid (9:1) and the mixture refluxed for 15 minutes. The product which separates on cooling to room temperature is recovered by filtration and dried (2.0 g.).

The compound exhibits ultraviolet absorption maxima in 0.01 N methanolic-HCl at 268 and 423 m$\mu$ (typical 5a,6-anhydro absorption) plus additional absorption in the 300–350 m$\mu$ region (modified A-ring).

By means of this procedure the remaining products of Example VI are converted to their respective 5a,6-anhydro derivatives with the exception, of course, of the 11a-halo derivatives.

EXAMPLE VIII

4-Hydroxyimino-4-Dedimethylaminotetracycline

Partially purified 4-oxo-4-dedimethylaminotetracycline-4,6-hemiketal (15 g.) is dissolved in 60 ml. of methanol, stirred for 20 minutes then filtered. To the filtrate there is added 30 g. of potassium bicarbonate and 6.3 g. of hydroxylamine hydrochloride. The mixture is stirred 15 minutes at room temperature, filtered, and the filter washed with methanol. The combined filtrate and wash liquors are diluted with 200 ml. of water and the pH adjusted to 2.0 with concentrated hydrochloric acid. The crude product precipitates and is removed by filtration (6.6 g.). Additional crude material (7.2 g.) is obtained by ether and ethyl acetate extractions of the mother liquor. The combined crude material is purified by dissolving in a mixture of toluene and isopropyl alcohol at the rate of 1 g. of crude in 3 ml. of toluene and 2 ml. of isopropyl alcohol, followed by immediate filtration. The pure material crystallizes upon standing and is dried at 50° C. in vacuo. It exhibits ultraviolet absorption maxima in 0.01 H methanolic-HCl at 309 and 360 m$\mu$.

EXAMPLE IX

4-Hydroxyimino-4-Dedimethylamino-5a,6-Anhydrotetracycline

Crude 4-hydroxyimino-4-dedimethylaminotetracycline (500 mg.) from Example VIII is dissolved in 3 ml. of 4% methanolic-HCl, the solution charcoaled and filtered. The charcoal filter cake is washed with methanol and the combined wash and mother liquors heated on a steam bath for 2–3 minutes, then allowed to stand at room temperature. The product which crystallizes on standing is recovered by filtration and dried in vacuo at room temperature. It exhibits typical anhydrotetracycline absorption in the ultraviolet region at 262 and 299 m$\mu$ in 0.01 H methanolic-HCl plus additional maxima at 422 m$\mu$. This latter maxima is due to the modified A-ring.

ANALYSIS

Found: C, 57.7; H, 4.1; N, 6.8. Calcd. for $C_{20}H_{16}N_2O_8 \cdot 0.5CH_3OH$: C, 57.5; H, 4.2; N, 6.6.

EXAMPLE X

Normal and Epi-4-Amino-4-Dedimethylamino-5a,6-Anhydrotetracycline

Method A - From 4-hydrazono-4-dedimethylaminotetracycline

4-Hydrazono-4-dedimethylaminotetracycline is slurried in 94 ml. of 1:1 solution of water and glacial acetic acid. Zinc dust (3.13 g.) is added and the mixture vigorously stirred at room temperature for 15 minutes. The mixture is filtered and the zinc cake washed with water-glacial acetic acid (1:1). The filtrate is freeze-dried, the residue slurried with 100 ml. of water, filtered, and the solid product (zinc complex) dried in air to give a yield of 3.0 g.

The crude zinc complex is taken up in a hot mixture of 15 ml. tetrahydrofuran and 0.5 ml. concentrated hydrochloric acid. The solution is filtered hot and the solution allowed to cool whereupon the product crystallizes. It is isolated by filtration and dried in vacuo at 50° C. for 48 hours. The yield from 950 mg. of crude zinc complex is 400 mg. It exhibits ultraviolet absorption maxima at 223, 272 and 423 m$\mu$ in 0.01 N methanolic-HCl, log $\epsilon$ 4.45, 4.71 and 3.93, respectively.

The same compound can also be prepared from the purified amphoteric 4-aminotetracycline by the same process. Other acids and other solvents can be used in this process.

Method B - From 4-hydroximino-4-dedimethylaminotetracycline

A mixture of crude 4-hydroxylimino-4-dedimethylaminotetracycline (3.5 g.), zinc dust (3.5 g.) and 104 ml. of 50% aqueous acetic acid is stirred at room temperature for 15 minutes. The mixture is then filtered and the filter cake washed with 50% aqueous acetic acid. The combined wash liquor and mother liquor are diluted with an equal volume of water then freeze-dried. The residue is slurried with ether, filtered and dried, then slurried with 100 ml. water. The solid is recovered by filtration and air-dried to give 5.5 g. of crude zinc complex.

The zinc complex is decomposed to give the desired product according to the procedure of Method A.

ANALYSIS

Found: C, 56.7; H, 5.1; N, 5.5; Cl, 7.1; $NH_2$, 3.2 Calcd. for $C_{20}H_{18}O_7N_2HCl\cdot(CH_2)_4O$: C, 56.9; H, 5.4; N, 5.5: Cl, 7.0: $NH_2$, 3.2

EXAMPLE XI

Method A - 4-Normal and 4-epi-4-amino-4-dedimethylaminotetracycline

To a slurry of 1.0 g. of 4-hydrazono-4-dedimethylaminotetracycline in 80 ml. of 50% aqueous methanol at room temperature, 2.0 g. of sodium hydrosulfite is added and the mixture stirred one hour. More sodium hydrosulfite (1.0 g.) is added and the stirring continued for an additional hour. A fourth gram of sodium hydrosulfite is then added and the stirring continued for another hour. The mixture is filtered, washed with 50% aqueous methanol and the filtrate evaporated in vacuo to remove the bulk of the methanol. The remaining aqueous solution is extracted with ethyl acetate to remove starting material and impurities of lower polarity than the desired product. The product is then extracted from the aqueous solution with n-butanol. The butanol extract is evaporated to dryness and the residue slurried with ether to give a solid product which is recovered by filtration.

The crude product thus obtained is purified by taking 2.67 g. of product (the combined product from several such preparations) in 100 ml. of dimethylformamide and adding 25 ml. of water. Crystallization begins immediately and after standing overnight at room temperature the product is recovered by filtration. It is washed with dimethylformamide until the wash liquor is colorless and then with other. The yield is 2.0 g.

The product exhibits absorption maxima in the ultraviolet region in 0.01 N methanolic-HCl at 262 and 359 m$\mu$: $E_{1\ cm}^{1\%}$ of 340 and 272, respectively. Both the normal and 4-epi compounds, the latter is the predominant isomer, are detected on paper chromatography in the system nitromethane:toluene:butanol:pyridine (20:10:5:3) as the mobile phase and McIlvaine's buffer, pH 3.5, as the stationary phase.

ANALYSIS

Found: C, 55.8; H, 5.9; N, 9.2. Calcd. for $C_{20}H_{20}O_8N_2\cdot1.5(CH_3)_2NCHO$: C, 55.9; H, 5.9; N, 9.3.

The products from both preparations show the typical tetracycline type ultraviolet absorption spectra in 0.01 N methanolic-HCl with maxima occurring at 260 and 360 m$\mu$, log $\epsilon$ 4.25 and 4.17.

Method B — From 4-hydroximino-4-dedimethylaminotetracycline

Repetition of Method A but using 4-hydroxyimino-4-dedimethylaminotetracycline as reactant produces the same product.

EXAMPLE XII

4-Normal and 4-Epi-4-Amino-4-Dedimethylaminotetracycline

A. To a mixture of 4-hydrazono-4-dedimethylaminotetracycline (429 mg.), 01 ml. concentrated hydrochloric acid, 2 ml. dimethylformamide, 5 ml. water and 5 ml. glacial acetic acid is added 50 mg. of platinum oxide (prehydrogenated) in 5 ml. water and 5 ml. glacial acetic acid. The slurry is hydrogenated for 3 hours at room temperature and 1 atmosphere hydrogen, filtered and the solids washed with dimethylformamide. The combined washings and filtrate are stripped to dryness to give a mixture of 4-epi and 4-normalamino-4-dedimethylaminotetracyclines.

B. Repetition of this procedure but using only dimethyl formamide (no water or acetic acid) as solvent produces the same product.

C. The 4-hydrazono-11a-chloro-4-dedimethylaminotetracycline of Example VI-C is reduced with excess zinc in 50% aqueous acetic acid to give the zinc complex of the normal and epi forms of 4-amino-4-dedimethylaminotetracycline.

EXAMPLE XIII

Isolation of Normal 4-Amino-4-Dedimethylaminotetracycline

Two-hundred mg. of the mixture of 4-amino-4-dedimethylaminotetracyclines of Example XII-A are taken up in 5 ml. of 4% aqueous sodium bicarbonate and warmed on a steam bath for 30 minutes. The solution is cooled and adjusted to pH 4.5 with dilute hydrochloric acid. The acid solution is then extracted with ethyl acetate to remove the 4-epi-amino-4-dedimethylaminotetracycline degradation products and then with n-butanol to extract the normal product. Evaporation of the n-butanol solution to dryness gives the desired 4-amino-4-dedimethylaminotetracycline.

EXAMPLE XIII

Isolation of Normal 4-Amino-4-Dedimethylaminotetracycline

Two-hundred mg. of the mixture of 4-amino-4-dedimethylaminotetracyclines of Example XII-A are taken up in 5 ml. of 4% aqueous sodium bicarbonate and warmed on a steam bath for 30 minutes. The solution is cooled and adjusted to pH 4.5 with dilute hydrochloric acid. The acid solution is then extracted with ethyl acetate to remove the 4-epi-amino-4-dedimethylaminotetracycline degradation products and then with n-butanol to extract the normal product. Evaporation of the n-butanol solution to dryness gives the desired 4-amino-4-dedimethylaminotetracycline.

EXAMPLE XIV

The products of Examples VI-B, VII and IX are similarly reduced to a mixture of 4-epi and normal 4-amino-4-dedimethylaminotetracyclines by the procedures of Examples XI and XII. In the case of the 5a,6-anhydro compounds zinc-acetic acid is used as reducing agent.

The following compounds are thus prepared:

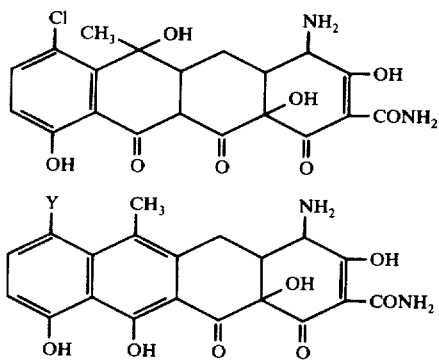

EXAMPLE XV

Reductive Amination of 4-Oxo-4-Dedimethylaminotetracycline-4,6-Hemiketal

A. To 300 mg. platinum oxide in 24 ml. of dimethylformamide (pre-reduced) is added a solution of 2.5 mg. of 4-oxo-4-dedimethylaminotetracycline-4,6-hemiketal and 1.22 mg. of magnesium chloride hexahydrate in 36 ml. dimethylformamide. Ammonium hydroxide (3 ml. of 28%) is added and the mixture hydrogenated at room temperature and 1 atmosphere hydrogen for 3 hours. The catalyst is filtered off, washed with dimethylformamide and the combined wash and filtrate solutions added to 700 ml. ether with stirring. The solid filtered off, washed with ether and dried is the crude ammonium magnesium complex of 4-epi and 4-normal amino-4-dedimethylaminotetracycline.

The complex is broken up according to the procedure of Example X to give the mixture of 4-amino-4-dedimethylamino-5a,6-anhydrotetracyclines.

B. Repetition of this procedure using equimolar amounts of zinc, cadmium, cobalt, copper, nickel and mangenese chlorides in place of magnesium chloride produces the same products.

EXAMPLE XVI

The procedure of Example XV-A is repeated but using aqueous methylamine in place of ammonium hydroxide to give 4-methylamino-4-dedimethylaminotetracycline consisting mainly of the 4-epi derivative with a small amount of the normal derivative.

Application of this procedure to the products of Example II and using the appropriate primary amine produces a mixture of the 4-epi and normal derivatives of the following compounds in which the 4-epi form predominates.

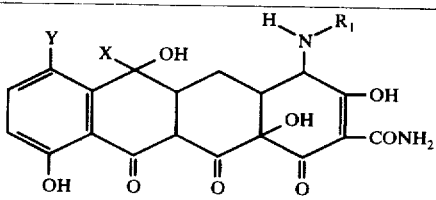

| Y | X | $R_1$ |
|---|---|---|
| H | $CH_3$ | $C_2H_5$ |
| H | $CH_3$ | $n\text{-}C_4H_9$ |
| H | $CH_3$ | $i\text{-}C_3H_7$ |
| H | $CH_3$ | $n\text{-}C_6H_{13}$ |
| H | $CH_3$ | $C_6H_5$ |
| H | $CH_3$ | $CH_2CH_2OH$ |
| H | $CH_3$ | $CH_2CH_2CH_2CH_2OH$ |
| H | $CH_3$ | $CH_2CHOHCH_3$ |
| H | $CH_3$ | $CH_2CH_2C_6H_5$ |
| Cl | $CH_3$ | $CH_3$ |
| Cl | $CH_3$ | $CH_2CH_2OH$ |
| Cl | $CH_3$ | $n\text{-}C_4H_9$ |

When the starting 4-oxo-4-dedimethylaminotetracycline-4,6-hemiketal bears a 7-chloro group, rhodium rather than platinum oxide is preferred as catalyst.

EXAMPLE XVII

The reductive amination products of Example XVI are transformed to their respective 5a,6-anhydro derivatives by the procedures of Example IV.

EXAMPLE XVIII

The sodium salt of 4-hydroxy-4-dedimethylamino-5a,6-anhydrotetracycline is prepared by dissolving this substance in water containing an equivalent amount of sodium hydroxide and lyophilizing the resulting solution. Similarly, the sodium, potassium, lithium, calcium, barium, strontium, aluminum and manganese salts of the tetracycline products of Examples I-XVII are prepared.

The acid salts, e.g. hydrochloride, sulfate, nitrate, acetate, propionate, hydrobromide, citrate, gluconate, phosphate and benzoate, of the basic products of this invention are prepared by dissolving the free base in water containing an equivalent amount of the desired acid and lyophilizing the resulting solution.

EXAMPLE XIX

A mixture of crude 4-epi-4-amino-4-dedimethylaminotetracycline (500 mg. containing a small amount of the normal 4-amino compound), methyl iodide (2.5 ml.) and 10 ml. tetrahydrofuran is refluxed overnight. The mixture is evaporated to dryness to give a mixture of normal and 4-epi-4-methylamino-4-dedimethylaminotetracycline hydroiodide.

Repetition of this procedure but using ethyl, n-butyl, n-hexyl, benzyl, phenethyl, cyclohexyl, 2-hydroxyethyl, 2-hydroxypropyl and 4-hydroxybutyl iodide in place of methyl iodide produces the corresponding 4-substituted amino-4-dedimethylaminotetracycline salts.

EXAMPLE XX

A mixture of 4-epi and 4-normal amino-4-dedimethylaminotetracycline (416 mg., 1 mM.), and 2 mM. of each of ethyl iodide and propylene oxide is refluxed in 20 ml. acetone overnight. The mixture is evaporated to dryness, the residue washed with ether and dried. The product comprises a mixture of 4-epi- and normal-4-diethylamino-4-dedimethylaminotetracycline.

Replacement of ethyl iodide by n-butyl, isopropyl and hexyl iodide produces the corresponding 4-dialkylamino-4-dedimethylaminotetracycline.

EXAMPLE XXI

The crude 4-epi- and normal-4-methylamino-4-dedimethylaminotetracycline product of Example XIX is taken up in water and the pH adjusted to 4.5. The acid solution is extracted with n-butanol and the butanol extract evaporated to dryness. The residue is then dissolved in 10 ml. tetrahydrofuran, n-butyl iodide (2 ml.) added and the mixture refluxed overnight. Evaporation to dryness gives 4-N-(n-butyl), N-methyl-amino-4-dedimethylaminotetracycline hydroiodide (4-epi- and normal configurations).

EXAMPLE XXII

Application of the procedures of Examples XIX to XXI on the 4-amino-compounds of Examples XIV produces the following products from the appropriate reactants.

| Y | X | $R_1$ | $R_2$ |
|---|---|---|---|
| H | $CH_3$ | $n\text{-}C_4H_9$ | $n\text{-}C_4H_9$ |
| H | $CH_3$ | $-CH_3$ | $-CH_2CH_2OH$ |
| H | $CH_3$ | $n\text{-}C_4H_9$ | $-CH_2CH_2OH$ |
| H | $CH_3$ | $-CH_3$ | $-(CH_2)_4OH$ |
| H | $CH_3$ | $-CH_2C_6H_5$ | $-C_2H_5$ |
| H | $CH_3$ | $-CH_3$ | $-CH_2CHOHCH_3$ |
| Cl | $CH_3$ | H | $-C_6H_{11}$ |
| Cl | $CH_3$ | $-CH_2C_6H_5$ | $-CH_2CH_2OH$ |
| Cl | $CH_3$ | $-CH_2CH_2C_6H_5$ | H |

| Y | X | $R_1$ | $R_2$ |
|---|---|---|---|
| H | $CH_3$ | $n\text{-}C_4H_9$ | H |
| H | $CH_3$ | $-C_2H_5$ | H |
| H | $CH_3$ | $-CH_3$ | H |
| H | $CH_3$ | $-CH_2C_6H_5$ | H |
| H | $CH_3$ | $-CH_3$ | $n\text{-}C_6H_{13}$ |
| H | $CH_3$ | H | $-CH_2CH_2OH$ |
| H | $CH_3$ | $-CH_3$ | $-(CH_2)_4OH$ |
| Cl | $CH_3$ | $CH_3$ | $-C_2H_5$ |
| Cl | $CH_3$ | $CH_3$ | $-CH_2CH_2OH$ |

The products are converted to the free base form by neutralization of the acid present and thence to various salts by the procedure of Example XVIII. The following salts are prepared: hydrochloride, acetate, citrate, benzoate, sodium, calcium, manganese, aluminum and magnesium.

EXAMPLE XXIII

4-Oxo-11a-Chloro-6-Deoxy-6-Demethyl-6-Methylene-4-Dedimethylaminotetracycline

4-Oxo-11a-chloro-4-dedimethylaminotetracycline-4,6-hemiketal is dissolved in liquid hydrogen fluoride (in a ratio of 2 g./15 ml.) at 0° C. After 15 minutes at this temperature the hydrogen fluoride is evaporated off to give the desired product.

In like manner, 4-oxo-6-deoxy-6-demethyl-6-methylene-4-dedimethylaminotetracycline and 4-oxo-11a-fluoro-6-deoxy-6-demethyl-6-methylene-4-dedimethylaminotetracycline are produced from 4-oxo-4-dedimethylaminotetracycline-4,6-hemiketal and 4-oxo-11a-fluoro-4-dedimethylaminotetracycline-4,6-hemiketal.

EXAMPLE XXIV

4-Hydrazono-11a-Chloro-6-Deoxy-6-Demethyl-6-Methylene-4-Dedimethylaminotetracycline Method A. A mixture of 10 g. of 4-oxo-11a-chloro-6-deoxy-6-demethyl-6-methylene-4-dedimethylaminotetracycline, 61 ml. of methanol, 20 g. of potassium bicarbonate, and 3.8 g. of powdered hydrazine dihydrochloride is stirred for 30 minutes at room temperature. The reaction mixture is then filtered and washed with methanol. 900 ml. of water containing 6 ml. of concentrated hydrochloric acid is slowly added to the mother liquor with stirring and the mixture allowed to stand. The precipitated product is recovered by filtration, washed with water and dried.

Repetition of this procedure but using hydroxylamine hydrochloride in place of hydrazine dihydrochloride produces 4-hydroxyimino-11a-chloro-6-deoxy-6-demethyl-6-methylene-4-dedimethylaminotetracycline.

Method B. 4-Hydrazono-11a-chloro-4-dedimethylaminotetracycline (product of Example VI-C) is dissolved in liquid hydrofluoric acid at 0° C. (2 g./15 ml.). After 15 minutes at 0° C. the mixture is evaporated to dryness to give the title compound as the hydrofluoride salt.

The following compounds are prepared from appropriate reactants by the procedure of Method A using the proper carbonyl group reagent in place of hydrazine dihydrochloride.

| Z | $R_3$ | Z | $R_3$ |
|---|---|---|---|
| H | $-NH_2$ | Cl | $-HNCH_3$ |
| H | $-OH$ | Cl | $-N(CH_3)_2$ |
| H | $-CH_3$ | Cl | $-N(C_2H_5)_2$ |
| H | $-NHCONH_2$ | Cl | $-NHCONH_2$ |
| H | $-NHC(NH)NH_2$ | Cl | $-NHC(NH)NH_2$ |
| H | $-NHCSNH_2$ | Cl | HN benzyl |
| H | $-HHC_6H_5$ | Cl | HN cyclohexyl |
| H | $-HN$ benzyl | Cl | $CH_3HC_6H_5$ |
| H | $-HN$ cyclohexyl | Cl | $N(C_6H_5)_2$ |
| H | $-HNC_4H_9$ | F | $-NH_2$ |
| H | $-N(C_2H_5)_2$ | F | $-OH$ |
| H | $-N(sec\text{-}C_4H_9)_2$ | F | $-NHCONH_2$ |
| H | 1-[4-(S-hydroxyethyl)piperazine] | F | $-NHCSNH_2$ |
| F | $-HN(i\text{-}C_3H_7)$ | F | $-H(CH_3)_2$ |
| F | $HNC_4H_9$ | F | $-HN$ benzyl |
|   |   | F | 1-[4-(S-hydroxyethyl)piperazine] |

EXAMPLE XXV

4-Epi and Normal 4-Amino-6-Deoxy-6-Demethyl-6-Methylene-4-Dedimethylaminotetracycline The 4-hydrazono product of Example XXIV (1 g.) is slurried in 10 ml. of 50% aqueous acetic acid and zinc dust (2 g.) added. The mixture is stirred vigorously for 15 minutes then filtered and the filter cake washed with 50% acetic acid and water. The product, as zinc complex, is recovered by freeze drying the mother liquor.

The zinc complex is converted to the p-toluene sulfonate salt by treatment with excess p-toluene sulfonic acid in water. The p-toluene sulfonate salt is recovered by filtration and dried in vacuo.

Similarly, the 4-hydroxyimino analog of Example XXIV is reduced to the same compound.

The free base is obtained by adjusting the pH of an aqueous solution of the p-toluene sulfonate salt to 5, filtering off and drying the product which separates.

The crystalline 5a,6-anhydro-4-amino-4-dedimethylaminotetracycline is obtained when the crude zinc complex (1 g.) is refluxed in 15 ml. of tetrahydrofuran containing 0.5 ml. concentrated HCl for 3 hours, then cooling to room temperature.

Similarly, the remaining product of Example XXIV are reduced to give the title product.

EXAMPLE XXVI

The product of Example XXIV as the base form is dissolved in methanol (10 mg./5 ml.) and a freshly prepared solution of sodium hydrosulfite added (40 mg. in 5 ml. water). After 15 minutes at room temperature the mixture is stripped of methanol and the residue extracted with n-butanol. Concentration of the n-butanol extract gives the 4-hydrazono-6-deoxy-6-demethyl-6-methylene-4-dedimethylaminotetracycline.

In like manner the remaining 11a-halo products of Example XXIV are converted to the corresponding deshalo compounds.

EXAMPLE XXVII

4-Hydroxy-6-Deoxy-6-Demethyl-6-Methylene-4-Dedimethylaminotetracycline

The 4-oxo product of Example XXIII (1.0 g.) is dissolved in 12 ml. methanol and a freshly prepared solution of 0.8 g. sodium hydrosulfite in 20 ml. water added. After stirring 40 minutes at room temperature the mixture is combined with 10 ml. water and 50 ml. ether. The ether extract is separated, the aqueous layer re-extracted with another 50 ml. ether and the combined ethereal solutions dried over sodium sulfate. Evaporation to dryness gives the crude product.

In like manner the remaining 4-oxo compounds of Example XXIII are reduced to the title compound.

EXAMPLE XXVIII

The product of Example XXV (500 mg.) is refluxed with methyl iodide (2.5 ml.) in tetrahydrofuran (10 ml.) for 15 hours. Evaporation of the mixture gives a mixture of normal and 4-epi-4-methylamino-6-deoxy-6-demethyl-6-methylenetetracycline hydroiodide.

Repetition of this procedure but using ethyl, n-butyl, n-hexyl, benzyl, phenethyl, cyclohexyl, 2-hydroxyethyl, 2-hydroxypropyl and 4-hydroxybutyl iodide in place of methyl iodide produces the corresponding 4-substituted amino-4-dedimethylaminotetracycline salts.

EXAMPLE XXIX

A mixture of 4-epi- and 4-normal amino-6-deoxy-6-demethyl-6-methylene-4-dedimethylaminotetracycline (1 mM.), and 2 mM. of each of ethyl iodide and propylene oxide is refluxed in 20 ml. acetone overnight. The mixture is evaporated to dryness, the residue washed with ether and dried. The product comprises a mixture of 4-epi- and normal-4-diethylamino-4-dedimethylaminotetracycline.

Replacement of ethyl iodide by n-butyl, isopropyl and hexyl iodide produces the corresponding 4-dialkylamino-4-dedimethylaminotetracyclines.

EXAMPLE XXX

The crude 4-epi- and normal-4-methylamino-6-deoxy-6-demethyl-6-methylene-4-dedimethylaminotetracycline product of Example XXVIII is taken up in water and the pH adjusted to 4.5. The acid solution is extracted with n-butanol and the butanol extract evaporated to dryness. The residue is then dissolved in 10 ml. tetrahydrofuran, n-butyl iodide (2 ml.) added and the mixture refluxed overnight. Evaporation to dryness gives 4-N-(n-butyl), N-methyl-amino-4-dedimethylaminotetracycline hydroiodide (4-epi- and normal configurations).

EXAMPLE XXXI

The sodium, potassium, calcium, barium, aluminum and magnesium salts of the products of Examples XXIII-XXX are prepared by the procedure of Example XVIII.

The acid salts, e.g. hydrochloride, sulfate, citrate, gluconate, citrate and benzoate, of the products of Example XXV, XXVIII-XXX are prepared according to the procedure of Example XVIII.

What is claimed is:

1. A compound selected from the group consisting of:

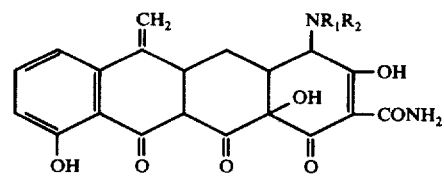

the acid addition salts and the alkali metal and alkaline earth metal salts thereof and

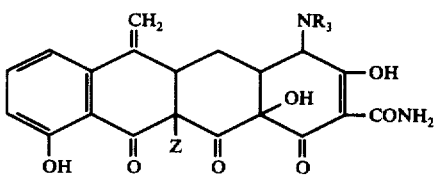

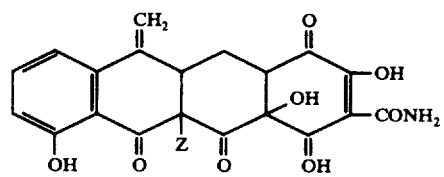

-continued and [structure with CH₂, OH, OH, OH, CONH₂, OH, O, O, O groups]

the alkali metal and alkaline earth metal salts thereof;

wherein $R_1$ is selected from the group consisting of hydrogen, benzyl, phenethyl, cyclohexyl and alkyl of from 2 to 6 carbon atoms;

$R_2$ is selected from the group consisting of hydrogen, alkyl of from 2 to 6 carbon atoms, and hydroxyalkyl of from 2 to 4 carbon atoms;

Z is selected from the group consisting of hydrogen, chloro and fluoro; and $R_3$ is selected from the group consisting of OH, $NHCONH_2$, $NHC(NH)NH_2$, $NHCSNH_2$, 4-(β-hydroxyethyl)piperazino, and $NR_4R_5$ wherein $R_4$ is selected from the group consisting of hydrogen, alkyl of from 1 to 6 carbon atoms, phenyl, benzyl and cyclohexyl and $R_5$ is selected from the group consisting of hydrogen, alkyl of from 1 to 6 carbon atoms, phenyl and benzyl.

2. The compound of the first structural formula of claim 1 wherein $R_1$ and $R_2$ are hydrogen.

* * * * *